(12) United States Patent
Arai

(10) Patent No.: US 11,478,306 B2
(45) Date of Patent: Oct. 25, 2022

(54) SHAPE ACQUIRING METHOD AND CONTROLLING METHOD FOR MEDICAL MANIPULATOR

(71) Applicant: OLYMPUS CORPORATION, Tokyo (JP)

(72) Inventor: Takeshi Arai, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 819 days.

(21) Appl. No.: 16/424,935

(22) Filed: May 29, 2019

(65) Prior Publication Data

US 2019/0307517 A1   Oct. 10, 2019

Related U.S. Application Data

(63) Continuation of application No. PCT/JP2016/088841, filed on Dec. 27, 2016.

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/30* (2016.02); *A61B 34/35* (2016.02); *A61B 34/70* (2016.02);
(Continued)

(58) Field of Classification Search
CPC ......... A61B 34/20; A61B 34/30; A61B 34/35; A61B 34/70; A61B 34/71; A61B 17/29; A61B 2017/00022; A61B 2017/00115; A61B 2017/00314; A61B 2017/00327; A61B 2017/0034; A61B 2034/2061; B25J 9/10
See application file for complete search history.

(56) References Cited

U.S. PATENT DOCUMENTS 4,443,698 A * 4/1984 Schiffner ........... G02B 6/02042
                                                      250/227.14
5,563,967 A * 10/1996 Haake .................... G01L 1/246
                                                            385/12
(Continued)

FOREIGN PATENT DOCUMENTS

CN      101496713 A    8/2009
EP      2 085 017 A1   8/2009
(Continued)

OTHER PUBLICATIONS

International Search Report and Written Opinion dated Mar. 29, 2016 received in PCT/JP2016/050436.
(Continued)

*Primary Examiner* — Bhavesh V Amin
(74) *Attorney, Agent, or Firm* — Scully, Scott, Murphy & Presser, P.C.

(57) ABSTRACT

A medical manipulator system according to the present invention is provided with: a manipulator; a manipulator channel; a route that extends along the manipulator channel; a shape sensor that detects shape information of the manipulator channel; a shape-sensor driving portion that causes the shape sensor to be driven; a manipulator driving portion that causes the manipulator to be driven; a positional-information calculating portion that calculates positional information of the shape sensor on the basis of a driven amount of the shape-sensor driving portion; a shape estimating portion that estimates a bent shape of the manipulator on the basis of the shape information of the manipulator channel and the positional information; a control-parameter calculating portion that calculates a control parameter of the manipulator from the bent-shape information; and a manipulator controller that controls the manipulator on the basis of the control parameter.

14 Claims, 12 Drawing Sheets

(51) Int. Cl.
*A61B 34/35* (2016.01)
*A61B 34/30* (2016.01)
*A61B 17/29* (2006.01)
*A61B 17/00* (2006.01)

(52) U.S. Cl.
CPC .............. *A61B 34/71* (2016.02); *A61B 17/29* (2013.01); *A61B 2017/00022* (2013.01); *A61B 2017/0034* (2013.01); *A61B 2017/00115* (2013.01); *A61B 2017/00314* (2013.01); *A61B 2017/00327* (2013.01); *A61B 2034/2061* (2016.02)

(56) References Cited

U.S. PATENT DOCUMENTS

| | | | |
|---|---|---|---|
| 5,798,521 A * | 8/1998 | Froggatt | G01B 11/18 250/227.14 |
| 5,840,024 A | 11/1998 | Taniguchi et al. | |
| 6,059,718 A | 5/2000 | Taniguchi et al. | |
| 6,256,090 B1 * | 7/2001 | Chen | G01V 1/3835 356/73.1 |
| 6,888,623 B2 * | 5/2005 | Clements | G01D 5/35341 356/73.1 |
| 6,999,852 B2 * | 2/2006 | Green | H04N 13/239 600/595 |
| 7,720,322 B2 * | 5/2010 | Prisco | A61B 34/35 385/12 |
| 8,105,230 B2 | 1/2012 | Honda et al. | |
| 8,918,212 B2 * | 12/2014 | Larkin | A61B 34/77 901/17 |
| 10,105,188 B2 * | 10/2018 | Larkin | G01L 5/226 |
| 10,111,711 B2 | 10/2018 | Farritor et al. | |
| 10,219,887 B2 * | 3/2019 | Johnson | A61F 2/0105 |
| 10,245,115 B2 * | 4/2019 | Froggatt | A61B 34/70 |
| 10,512,510 B2 * | 12/2019 | Blumenkranz | A61B 34/20 |
| 10,537,397 B2 * | 1/2020 | Larkin | B25J 9/1689 |
| 10,682,070 B2 * | 6/2020 | Duindam | A61B 34/20 |
| 10,791,908 B2 * | 10/2020 | Au | A61B 1/0016 |
| 10,898,256 B2 | 1/2021 | Yates et al. | |
| 10,939,826 B2 * | 3/2021 | Glynn | A61M 1/84 |
| 10,939,972 B2 * | 3/2021 | Au | B25J 9/1689 |
| 11,116,590 B2 * | 9/2021 | Larkin | B25J 18/06 |
| 11,324,393 B2 * | 5/2022 | Froggatt | A61B 1/00167 |
| 2002/0097960 A1 * | 7/2002 | Greenaway | G01D 5/3538 385/36 |
| 2006/0013523 A1 * | 1/2006 | Childers | G02B 6/02042 385/12 |
| 2007/0116415 A1 | 5/2007 | Kobayashi | |
| 2007/0151390 A1 * | 7/2007 | Blumenkranz | A61B 34/71 74/490.06 |
| 2007/0156019 A1 * | 7/2007 | Larkin | A61B 1/009 600/104 |
| 2007/0197939 A1 * | 8/2007 | Wallace | A61M 25/01 600/587 |
| 2008/0065110 A1 | 3/2008 | Duval et al. | |
| 2009/0038413 A1 * | 2/2009 | Seibold | G01L 5/166 73/862.043 |
| 2009/0088897 A1 * | 4/2009 | Zhao | A61B 34/30 700/250 |
| 2009/0138025 A1 | 5/2009 | Stabler et al. | |
| 2009/0157092 A1 * | 6/2009 | Blumenkranz | A61B 34/37 73/800 |
| 2009/0192524 A1 | 7/2009 | Itkowitz et al. | |
| 2009/0198104 A1 | 8/2009 | Sugiyama | |
| 2009/0299344 A1 | 12/2009 | Lee et al. | |
| 2009/0324161 A1 * | 12/2009 | Prisco | G01L 1/246 385/12 |
| 2010/0030063 A1 | 2/2010 | Lee et al. | |
| 2010/0042077 A1 | 2/2010 | Okada | |
| 2010/0099951 A1 | 4/2010 | Laby et al. | |
| 2010/0125284 A1 | 5/2010 | Tanner et al. | |
| 2010/0202727 A1 | 8/2010 | Prisco | |
| 2010/0228265 A1 | 9/2010 | Prisco | |
| 2010/0236352 A1 | 9/2010 | Iida | |
| 2010/0318100 A1 | 12/2010 | Okamoto et al. | |
| 2011/0202069 A1 | 8/2011 | Prisco et al. | |
| 2012/0132009 A1 | 5/2012 | Prisco | |
| 2013/0204124 A1 | 8/2013 | Duindam et al. | |
| 2013/0261392 A1 | 10/2013 | Yamamoto et al. | |
| 2014/0330080 A1 | 11/2014 | Laby et al. | |
| 2014/0343416 A1 | 11/2014 | Panescu et al. | |
| 2015/0127019 A1 | 5/2015 | Komuro et al. | |
| 2015/0223670 A1 | 8/2015 | Fujita et al. | |
| 2016/0151121 A1 | 6/2016 | Prisco et al. | |
| 2016/0157944 A1 | 6/2016 | Prisco et al. | |
| 2016/0338784 A1 | 11/2016 | Hatakeyama et al. | |
| 2016/0346054 A1 | 12/2016 | Hatakeyama et al. | |
| 2016/0360951 A1 | 12/2016 | Hane | |
| 2017/0014194 A1 | 1/2017 | Duindam et al. | |
| 2017/0051026 A1 | 2/2017 | Doolan et al. | |
| 2017/0071683 A1 | 3/2017 | Prisco et al. | |
| 2017/0151026 A1 | 6/2017 | Panescu et al. | |
| 2017/0319049 A1 | 11/2017 | Laby et al. | |
| 2019/0021796 A1 | 1/2019 | Timperley et al. | |
| 2019/0029762 A1 | 1/2019 | Iida et al. | |
| 2019/0307517 A1 * | 10/2019 | Arai | A61B 34/71 |
| 2020/0289142 A1 | 9/2020 | Brisson et al. | |
| 2020/0397457 A1 | 12/2020 | Kim et al. | |
| 2020/0405418 A1 | 12/2020 | Grubbs et al. | |
| 2021/0015519 A1 | 1/2021 | Meglan et al. | |
| 2021/0015572 A1 | 1/2021 | Gomez et al. | |

FOREIGN PATENT DOCUMENTS

| | | |
|---|---|---|
| EP | 2 324 789 A1 | 5/2011 |
| EP | 2 647 327 A1 | 10/2013 |
| EP | 2 912 987 A1 | 9/2015 |
| EP | 3 108 797 A1 | 12/2016 |
| EP | 3 111 877 A1 | 1/2017 |
| JP | H03-295534 A | 12/1991 |
| JP | H08-107875 A | 4/1996 |
| JP | 2001-087281 A | 4/2001 |
| JP | 2004-000551 A | 1/2004 |
| JP | 3850377 B2 | 11/2006 |
| JP | 2007-143600 A | 6/2007 |
| JP | 2008-289556 A | 12/2008 |
| JP | 2009-131406 A | 6/2009 |
| JP | 2010-223724 A | 10/2010 |
| JP | 2011-019551 A | 2/2011 |
| JP | 2011-62291 A | 3/2011 |
| JP | 2012-115521 A | 6/2012 |
| JP | 2013-519432 A | 5/2013 |
| JP | 2014-83289 A | 5/2014 |
| JP | 2014-117446 A | 6/2014 |
| JP | 2015-505507 A | 2/2015 |
| JP | 2015-154814 A | 8/2015 |
| JP | 2015-159926 A | 9/2015 |
| JP | 2015-181643 A | 10/2015 |
| JP | 2016-129715 A | 7/2016 |
| JP | 2016-523592 A | 8/2016 |
| WO | 2008/094949 A2 | 8/2008 |
| WO | 2008/143218 A1 | 11/2008 |
| WO | 2010/055745 A1 | 5/2010 |
| WO | 2011/100124 A1 | 8/2011 |
| WO | 2013/116140 A1 | 8/2013 |
| WO | 2014/186715 A1 | 11/2014 |
| WO | 2015/119935 A1 | 8/2015 |
| WO | WO 2015/146712 A1 | 10/2015 |
| WO | 2017/119112 A1 | 7/2017 |
| WO | 2017/175320 A1 | 10/2017 |

OTHER PUBLICATIONS

International Search Report dated Mar. 28, 2017 received in PCT/JP2016/088841.

Japanese Office Action dated Nov. 12, 2019 in Japanese Patent Application No. 2017-559999.

Japanese Office Action dated Mar. 10, 2020 in Japanese Patent Application No. 2018-510161.

(56) References Cited

OTHER PUBLICATIONS

D. B. Camarillo, et al., "Vision based 3-D shape sensing of flexible manipulators", IEEE, pp. 2940-2947, DOI: https://doi.org/10.1109/ROBOT.2008.4543656.
Y. Domae, et al., "3D measurement of flexible objects by robust motion stereo", IEEE, pp. 740-743, DOI: https://doi.org/10.1109/SICE.2007.4421080.
A. Vandini, et al., "Vision-based motion control of a flexible robot for surgical applications", IEEE, pp. 6205-6211, DOI: 10.1109/ICRA.2014.6907774.
Office Action dated Aug. 15, 2016 in U.S. Appl. No. 14/594,511.
Office Action dated Jan. 23, 2017 in U.S. Appl. No. 14/594,511.
Office Action dated Feb. 1, 2021 in U.S. Appl. No. 16/148,256.
Chinese Office Action dated Apr. 18, 2016 received in 201380037576.9.
International Search Report and Written Opinion of the International Searching Authority dated Oct. 22, 2013 received in PCT/JP2013/070349.
Japanese Office Action dated Jun. 9, 2015 received in 2014-528119.
Japanese Decision to Grant a Patent dated Dec. 1, 2015 received in 2014-528119.
Extended Search Report dated Mar. 4, 2016 received in 13825274.7.
International Search Report and Written Opinion dated Jul. 5, 2016 issued in PCT/JP2016/061196.
Written Opinion dated Mar. 28, 2017 issued in PCT/JP2016/088841.

\* cited by examiner

SHAPE ACQUIRING METHOD AND CONTROLLING METHOD FOR MEDICAL MANIPULATOR

CROSS-REFERENCE TO RELATED APPLICATIONS

This is a continuation of International Application PCT/JP2016/88841, with an international filing date of Dec. 27, 2016, which is hereby incorporated by reference herein in its entirety.

The present invention relates to a shape acquiring method and a controlling method for a medical manipulator.

BACKGROUND ART

There is a known medical manipulator system with which an affected part of the body is treated by inserting a medical manipulator into the body of a patient via a forceps channel or the like in an endoscope that is inserted into a body cavity of the patient (for example, see U.S. Pat. No. 7,720,322, Specification).

With the medical manipulator system of Patent Literature 1, kinematic shape information of the manipulator, that is, information concerning joint angles of the manipulator, is estimated on the basis of information concerning bending detected by an optical fiber sensor and information concerning a kinematic model.

SUMMARY OF INVENTION

An aspect of the present invention is a medical manipulator system including: an elongated manipulator that has a flexible portion and that has one or more joints at a distal end; a manipulator channel that passes through the manipulator; a route that is provided in the manipulator channel along a longitudinal direction; a shape sensor that is provided so as to be capable of moving in an interior of the route, and that has one or more detection points that detect shape information of the manipulator channel; a shape-sensor driving portion that causes the shape sensor to be driven forward and backward along the longitudinal direction of the route; a manipulator driving portion that drives the manipulator; and a controller that controls the manipulator and the shape sensor, wherein the controller is provided with a positional-information calculating portion that calculates longitudinal-direction positional information of the shape sensor on the basis of a driven amount of the shape-sensor driving portion, a shape estimating portion that estimates a bent shape of the manipulator on the basis of the detected shape information of the manipulator channel and the calculated longitudinal-direction positional information of the shape sensor, a control-parameter calculating portion that calculates a control parameter of the manipulator from the estimated bent-shape information of the manipulator, and a manipulator controller that controls the manipulator on the basis of the calculated control parameter.

In the above-described aspect, the shape estimating portion may compare the shape information of the manipulator channel detected by the shape sensor and the shape information of the same manipulator channel detected (N+1) cycles (N≥0) earlier, and may update the shape information of the manipulator in the case in which the difference therebetween is equal to or greater than a first threshold.

In the above-described aspect, the shape-sensor driving portion may be provided with: a motor that is disposed in the vicinity of a base end of the manipulator and that generates a motive power for driving, by means of rotational driving thereof, the shape sensor forward and backward; and a guiding member that is disposed in the vicinity of a distal end of the manipulator and that guides the shape sensor by winding a portion thereof about the guiding member, wherein the shape sensor may be moved forward and backward by pulling and feeding out the shape sensor in association with the rotational driving of the motor.

In the above-described aspect, a pulling wire having a diameter that is smaller than that of the shape sensor may be connected to a distal end of the shape sensor, and the shape-sensor driving portion may be provided with: a motor that is disposed in the vicinity of a base end of the manipulator and that generates a motive power for driving the shape sensor forward and backward via the pulling wire by means of the rotational driving thereof, and a guiding member that is disposed in the vicinity of a distal end of the manipulator and that guides the pulling wire by winding a portion thereof about the guiding member, wherein the shape sensor may be moved forward and backward by pulling and feeding out the shape sensor in association with the rotational driving of the motor.

The above-described aspect may be provided with an auxiliary shape sensor that is disposed parallel to the shape sensor and that is connected to an end portion of the pulling wire on the opposite side from the side at which the shape sensor is connected.

The above-described aspect may be provided with, between the shape sensor and the guiding member, a stopper that prevents the shape sensor from intruding into the guiding member.

The above-described aspect may be provided with a pressure receiving member that is provided at a distal end of the shape sensor and that is capable of expanding to substantially the same diameter as the inner diameter of the route, wherein the shape-sensor driving portion may be provided with a pressuring member for driving the shape sensor forward and backward by applying pressure to the pressure receiving member in the longitudinal direction.

In the above-described aspect, the shape estimating portion may determine that there is an abnormality in the case in which the shape information of the manipulator channel detected by the shape sensor is equal to or greater than a second threshold; and may cause the shape sensor to detect the shape information of the manipulator channel again.

In the above-described aspect, the manipulator controller may compare the control parameter of the manipulator calculated by the control-parameter calculating portion and the control parameter of the manipulator calculated one cycle earlier; and, in the case in which the difference therebetween is equal to or greater than a third threshold, may cause the manipulator driving portion to output a corrected control parameter that is corrected by a high-frequency cut-off filter stored in the manipulator controller.

In the above-described aspect, the manipulator controller may compare the controller of the manipulator calculated by the control-parameter calculating portion and the control parameter of the manipulator calculated one cycle earlier; and, in the case in which the difference therebetween is greater than a fourth threshold, may determine that there is an abnormality, and may cause the shape sensor to detect the shape information of the manipulator channel again.

The above-described aspect may be provided with a warning portion that issues a warning to an operator indicating the occurrence of an abnormal state in the case in which the number of times the determination that there is an abnormality is detected reaches or exceeds a predetermined number of times.

In the above-described aspect, the manipulator driving portion may control the joints on the basis of the shape information of the manipulator acquired by the shape sensor.

An aspect of the present invention is a bent-shape estimating method for a medical manipulator, said method including: a shape-sensor driving step of moving a shape sensor having one or more detection points forward and backward along a longitudinal direction of a manipulator channel in which an elongated manipulator that has a flexible portion having one or more joints at a distal end thereof is disposed; a positional-information calculating step of calculating longitudinal-direction positional information of the shape sensor on the basis of a driven amount of the shape sensor; and a shape estimating step of estimating the bent shape of the manipulator on the basis of the detected shape information of the shape sensor and the shape information of the manipulator channel detected by the shape sensor at the calculated longitudinal-direction positions of the shape sensor.

An aspect of the present invention is a controlling method for a medical manipulator, said method including: a control-parameter calculating step of calculating a control parameter of a manipulator from the bent shape of the manipulator estimated by means of the bent-shape estimating method for a medical manipulator according to claim 13; and a manipulator controlling step of controlling the manipulator on the basis of the calculated control parameter.

DESCRIPTION OF EMBODIMENT

A medical manipulator system 1 and a shape acquiring method and a controlling method for a manipulator 2 according to an embodiment of the present invention will be described below with reference to the drawings.

Figure 1:
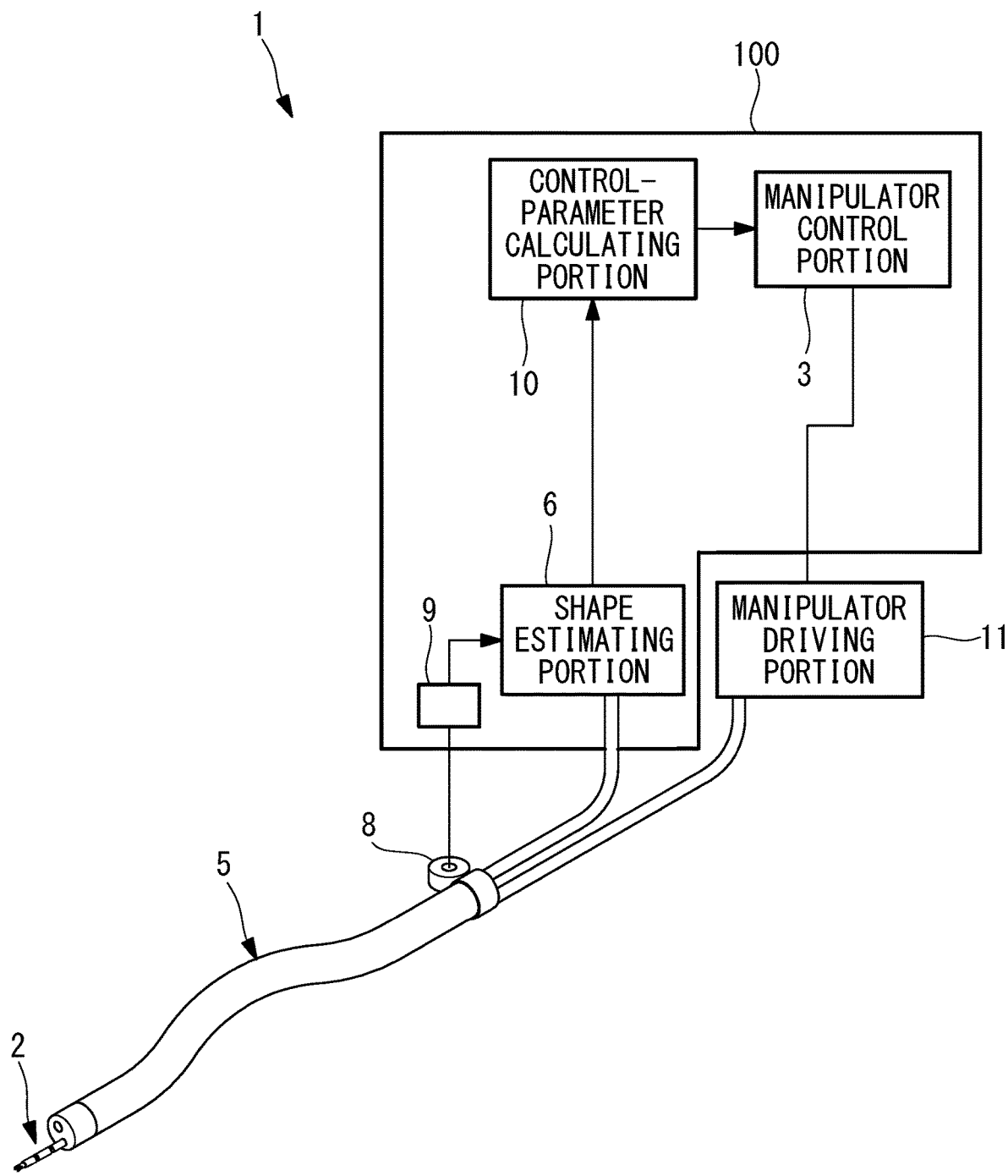
FIG. 1 is an overall configuration diagram showing a medical manipulator system according to an embodiment of the present invention.
Figure 2:
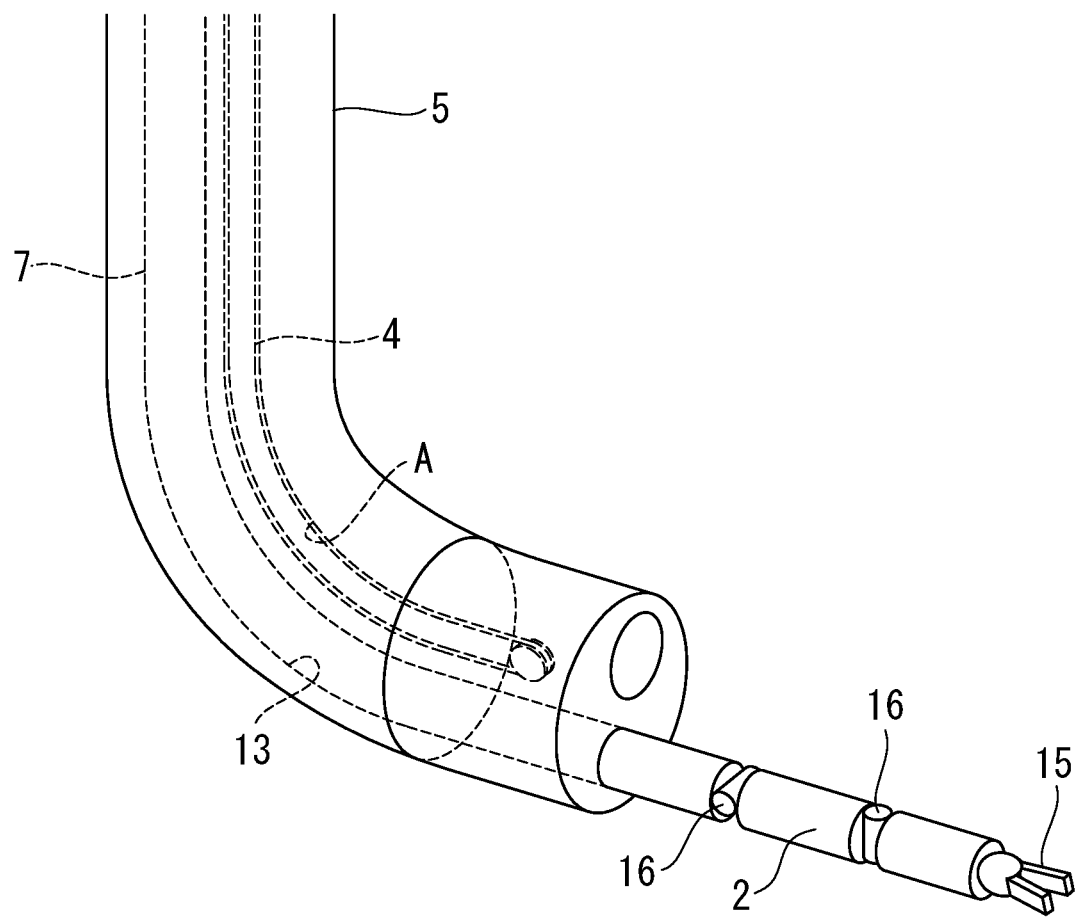
FIG. 2 is a partial enlarged view showing a distal-end portion of the medical manipulator in FIG. 1.
Figure 3:
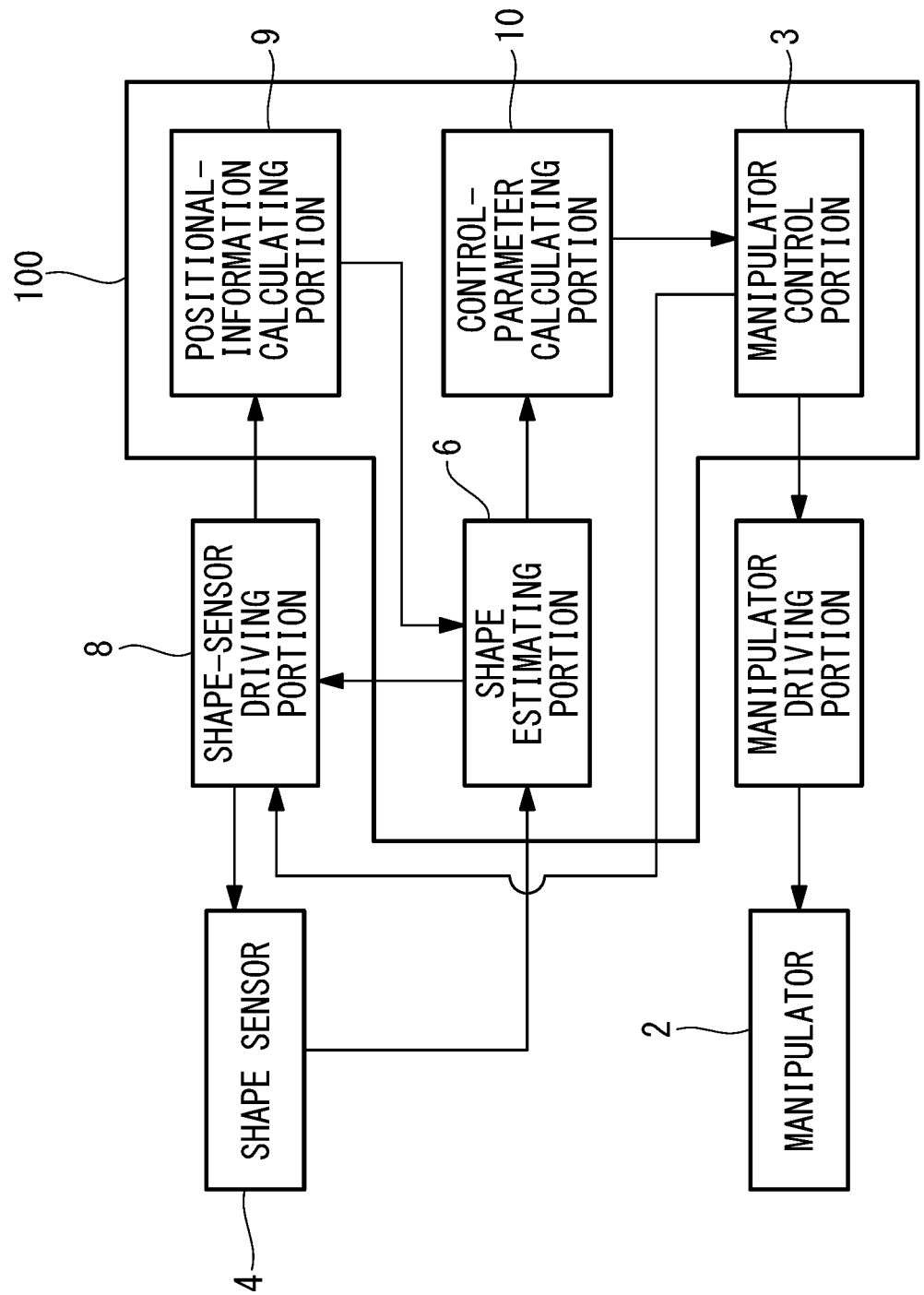
FIG. 3 is a functional block diagram of the medical manipulator system in FIG. 1.

As shown in FIGS. 1 to 3, the medical manipulator system 1 according to this embodiment is provided with: an overtube 5 that is a long, thin tube formed of a material possessing flexibility; the manipulator 2, which is elongated and is inserted into a manipulator channel 13 provided in the overtube 5 and that has one or more joints at a distal end thereof; shape sensors 4 that are inserted into a route A provided parallel to a longitudinal direction of the manipulator channel 13 into which the manipulator 2 is inserted, and that detect the radii of curvature (shape information) of the manipulator channel 13; a shape-sensor driving portion 8 that drives the shape sensors 4 forward and backward along the longitudinal direction in the route A; and a control portion (controller) 100 that controls the manipulator 2 and the shape sensors 4.

The control portion 100 is provided with: a positional-information calculating portion 9 that calculates information concerning the positions of the shape sensors 4 in the longitudinal direction on the basis of the driven amount (inserted amount) of the shape-sensor driving portion 8; a shape estimating portion 6 that estimates the bent shape of the manipulator 2 on the basis of the detected shape information (radii of curvature) of the manipulator channel 13 and the calculated longitudinal-direction positional information of the shape sensors 4; a control-parameter calculating portion 10 that calculates a control parameter of the manipulator 2 from the estimated bent-shape information of the manipulator 2; and a manipulator control portion (manipulator controller) 3 that controls the manipulator 2 on the basis of the calculated control parameter.

The shape-sensor driving portion 8 is provided with: a motor 18 that is disposed in the vicinity of the base end of the manipulator 2 and that drives, by means of rotational driving, the shape sensors 4 forward and backward; and a guiding member 17 that is disposed in the vicinity of the distal end of the manipulator 2 and that guides the shape sensors 4 by winding a portion of the shape sensors 4 therearound.

As shown in FIG. 2, the manipulator 2 is provided with: a long, thin flexible portion 7; a treating portion 15, such as gripping forceps, that is disposed at a distal end of the flexible portion 7; and joints 16 that change the attitude of the treating portion 15. As shown in FIG. 1, at a base end of the flexible portion 7, a manipulator driving portion 11 that drives the manipulator 2 is provided, and generates a motive power for driving the manipulator 2 on the basis of an instruction from the manipulator control portion 3, described later. The manipulator driving portion 11 is provided with a motor (not shown) that generates the motive power, and operates, by means of the rotation of the motor, the treating portion 15 and the joints 16 via motive-power transmitting members such as wires.

Figure 4A:
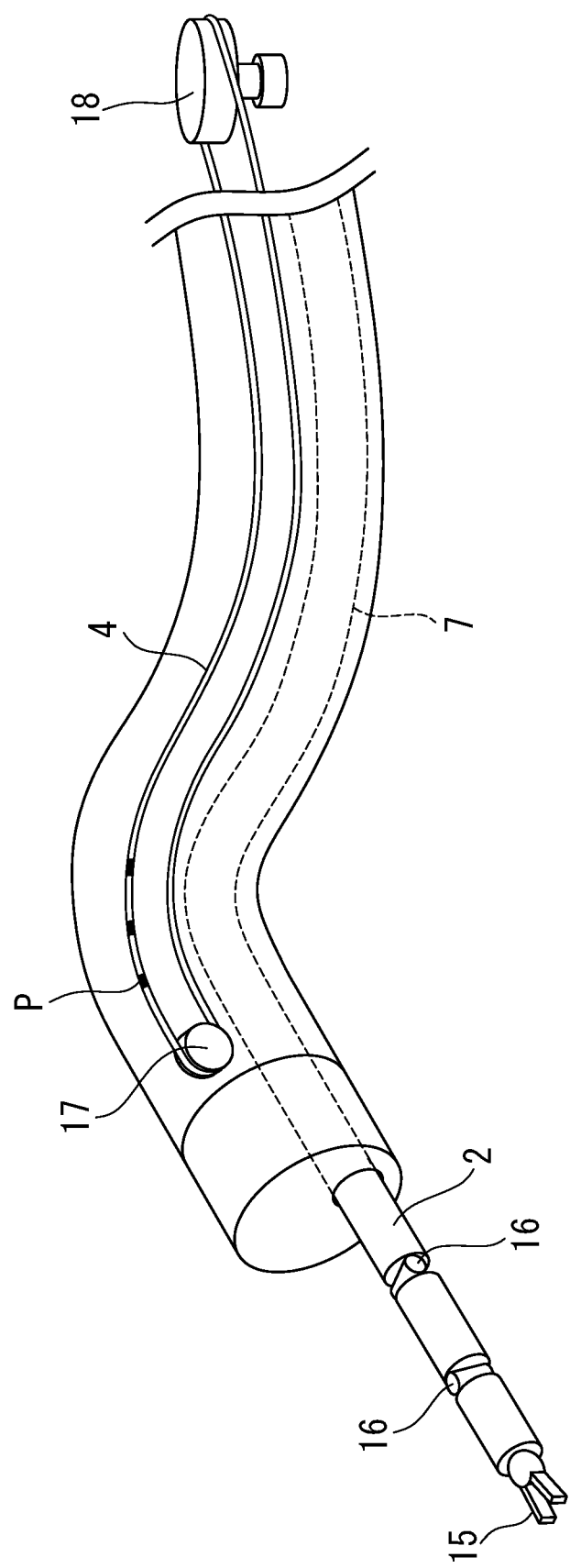
FIG. 4A is a diagram showing examples of a shape sensor and a shape-sensor driving portion employed in the medical manipulator system in FIG. 1.

The shape sensors 4 are, for example, sensors formed of long, thin elongated members that possess flexibility, such as optical fiber sensors, and detect, at one or more detection points P provided along the longitudinal direction, signals in accordance with the radii of curvature in a direction along a plane that includes the longitudinal axes of the shape sensors 4. As shown in FIG. 2, the shape sensors 4 are inserted into the route A that is provided parallel to the longitudinal direction of the manipulator channel 13, and the shape-sensor driving portion 8 provided at the base end of the shape sensors 4 is capable of driving, by means of rotational driving thereof, the shape sensors 4 forward and backward along the longitudinal direction of the route A. More specifically, as shown in FIG. 4A, the shape sensors 4 formed of the elongated members are folded back after being wound about the guiding member 17 disposed in the vicinity of the distal end of the manipulator 2, and the base-end portion thereof is connected to the motor 18 disposed in the vicinity of the base end of the manipulator 2. In other words, the shape sensors 4 are formed in a loop shape between the motor 18 and the guiding member 17 of the shape-sensor driving portion 8, and the shape sensors 4 are moved forward and backward as a result of being pulled and fed out between the motor 18 and the guiding member 17 in association of the rotational driving of the motor 18.

The positional-information calculating portion 9 calculates the longitudinal-direction movement amount (longitudinal-direction positional information) of the shape sensors 4 on the basis of the driven amount (inserted amount) of the shape sensors 4 inserted by the shape-sensor driving portion 8. It is possible to calculate the longitudinal-direction movement amount of the shape sensors 4, for example, by converting the rotation amount of the motor 18.

Alternatively, another method may be employed such as a method in which a rotating member (not shown), such as a roller, that comes into contact with outer surfaces of the shape sensors 4 and that is rotated by means of the movement of the shape sensors 4 in the longitudinal direction is provided, and the longitudinal-direction movement amount of the shape sensors 4 is calculated on the basis of the rotation amount of this rotating member.

While the shape sensors 4 are being moved in the route A that is provided parallel to the direction along the longitudinal direction of the manipulator channel 13 in which the manipulator 2 is disposed, the shape estimating portion 6 estimates the bent shape of the route A on the basis of the inserted amount of the shape sensors 4 calculated by the positional-information calculating portion 9 and the signals in accordance with the radii of curvatures detected by the shape sensors 4. Because the route A into which the shape sensors 4 are inserted is provided parallel to the longitudinal direction of the manipulator channel 13 into which the manipulator 2 is inserted, when the manipulator 2 is inserted into the manipulator channel 13, the shape of the flexible portion 7 of the manipulator 2 changes in conformity to the shape of the manipulator channel 13, and the shapes of the shape sensors 4 inserted into the route A change.

Therefore, the shape information of the route A and the shape information of the manipulator channel 13 are nearly identical to each other, and thus, it is possible to consider the bent shape of the route A as the bent shape of the manipulator channel 13.

The route A into which the shape sensors 4 are inserted may be, in addition to a channel that is provided in an endoscope or an overtube and into which the manipulator 2 is inserted, a channel provided in the manipulator 2 itself or an internal hole or the like of a tube disposed so as to run along the outer surface of the manipulator 2, and, in particular, in the case in which an affected part in the body is treated by inserting the manipulator 2 into the winding body cavity of a patient, the route A may be an arbitrary route that represents the bent shape of the manipulator 2 in the state of being inserted into the body cavity.

The control-parameter calculating portion 10 calculates the control parameter of the manipulator 2 from the information concerning the bent shape of the manipulator 2 estimated by the shape estimating portion 6. The manipulator control portion 3 controls the manipulator 2 on the basis of the control parameter of the manipulator 2 calculated by the control-parameter calculating portion 10.

The operation of the medical manipulator system 1 according to this embodiment, thus configured, will be described below.

In order to treat an affected part in a body cavity of a patient by using the medical manipulator system 1 according to this embodiment, first, the overtube 5 is inserted along the winding body cavity of the patient until reaching the vicinity of the affected part. Because the overtube 5 possesses flexibility, the overtube 5 bends in conformity to the shape of the body cavity of the patient. Then, the manipulator 2, which has been selected in accordance with the treatment, is inserted into the manipulator channel 13 provided in the overtube 5.

Next, the shape sensors 4 are inserted into the route A provided in the overtube 5. Then, while driving, by means of the motor 18, the shape sensors forward and backward in the longitudinal direction between the motor 18 and the guiding member 17, measurements of the radii of curvature at the individual positions of one or more detection points P and movement of the shape sensors 4 in the longitudinal direction are repeated, and the bent shape of the manipulator channel 13 is estimated by the shape estimating portion 6 on the basis of data in which the obtained information concerning the multiple radii of curvature and information concerning the longitudinal direction positions are associated with each other. By doing so, it is possible to estimate the bent shape of the manipulator channel 13 by tracing the bent shape by means of the shape sensors 4.

Because the bent shape of the manipulator channel 13 is estimated in this way, it is possible to enhance the operability of the manipulator 2 even in the state in which the manipulator 2 is inserted into the manipulator channel 13, because the manipulator 2 is controlled by the manipulator control portion 3 on the basis of the bent shape estimated by the manipulator channel 13.

In the case in which the overtube 5 is moved in order to treat a different affected part from a state in which one affected part is being treated, the posture of the patient is changed, a movement occurs in an organ, or the like, the shape of the body cavity of the patient changes in some cases, and the overtube 5 is also bent in conformity to the changed shape of the body cavity. In such a case, the bent shape of the manipulator channel 13 is estimated again while moving the shape sensors 4 forward and backward in the longitudinal direction in the route A, and the operation to bend the manipulator 2 in accordance with the estimated bent shape of the manipulator channel 13 is repeated.

As has been described above, with the medical manipulator system 1 according to this embodiment, it is possible to control the manipulator 2 in the manipulator channel 13 with the shape sensors 4 being disposed in the route A of the overtube 5 without removing and inserting the shape sensors 4 even in the case in which the affected part is moved or the posture of the patient or the like is changed while performing a procedure.

With the medical manipulator system 1 according to this embodiment, because the bent shape of the manipulator channel 13 is estimated by detecting multiple items of the shape information at the individual positions via one or more detection points P while moving the small number of shape sensors 4 in the longitudinal direction of the route A, a large number of shape sensors 4 is not necessary, and thus, there is an advantage in that it is possible to measure the bent shape of the manipulator 2 along the longitudinal direction by using the minimum number of shape sensors 4.

Because it is possible to perform a procedure without removing the shape sensors 4 from the route A and inserting the shape sensors 4 thereinto, it is possible to estimate, in real time, the bent shape of the manipulator 2 along the longitudinal direction when disposed in the manipulator channel 13.

Because the manipulator 2 is controlled on the basis of the control parameter calculated from the information concerning the estimated shape of the manipulator 2, there is a advantage in that it is possible to achieve good control of the manipulator 2 regardless of the shape of the flexible portion 7 by compensating for the attenuation of the driving force of the manipulator 2 and interference of the joints.

In this embodiment, the shape estimating portion 6 may compare the detected shape information of the manipulator channel 13 and the shape information of the manipulator channel 13 detected in advance, and may update the shape information in the case in which the difference therebetween is equal to or greater than a predetermined threshold.

Figure 5:
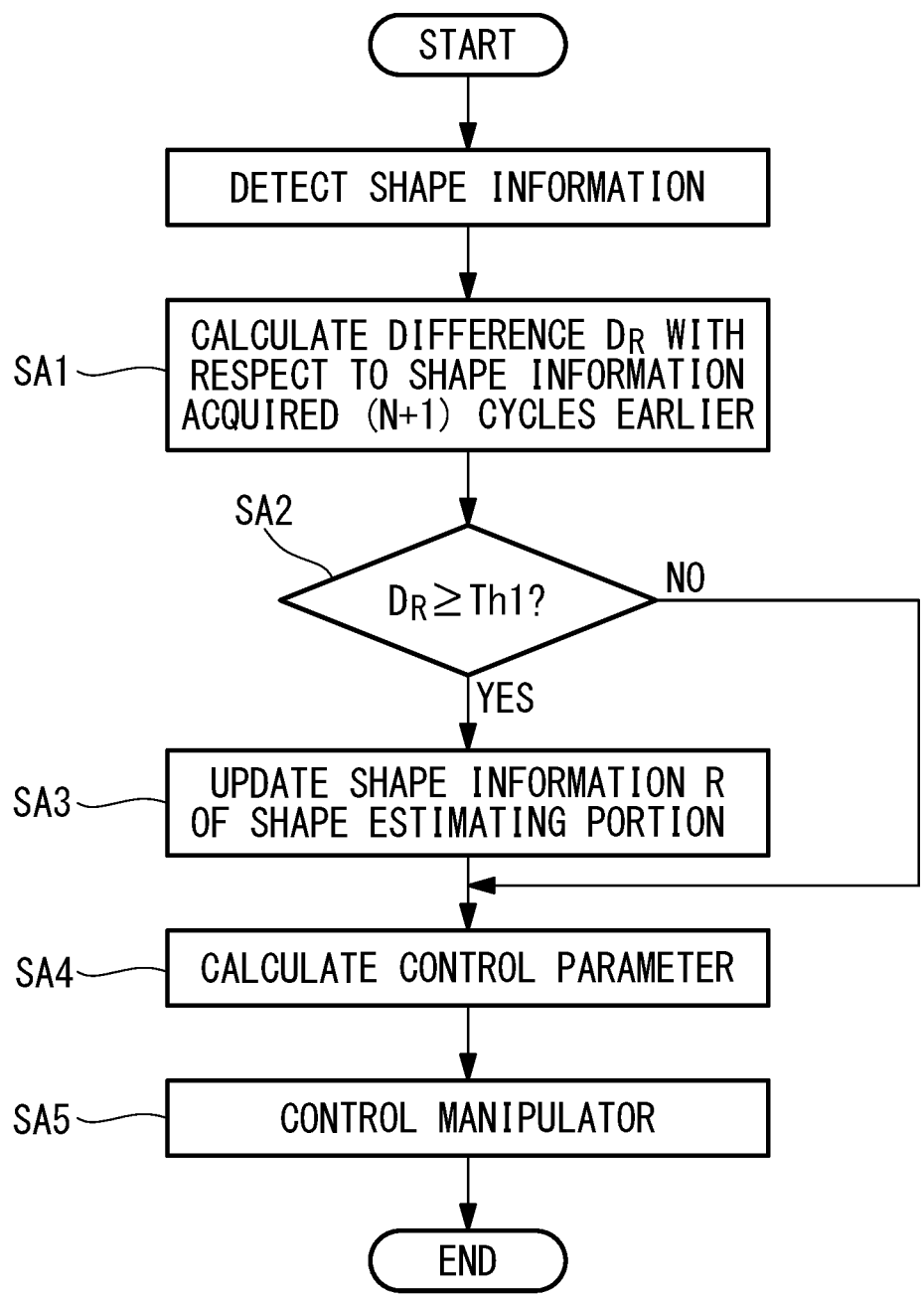
FIG. 5 is a flowchart showing a medical-manipulator controlling method according to the embodiment of the present invention.

Specifically, as shown in FIG. 5, the shape information of the manipulator channel 13 detected by the shape sensors 4 and the shape information of the manipulator channel 13 detected (N+1) cycles (N≥0) earlier are compared (step SA1), and, in the case in which this difference $D_R$ is equal to or greater than a first threshold Th1 (step SA2), it is determined that the shape of the manipulator channel 13 has changed and the shape information of the manipulator 2 is updated (step SA3). Then, the control-parameter calculating portion 10 calculates the control parameter of the manipulator 2 on the basis of the updated shape information (step SA4), and the manipulator control portion 3 controls the manipulator 2 on the basis of this calculated control parameter (step SA5).

In the case in which the difference $D_R$ between the shape information of the manipulator channel 13 and the shape information of the manipulator channel 13 detected (N+1) cycles (N≥0) earlier is equal to or less than the first threshold Th1 (step SA2), the original shape information is transmitted to the control-parameter calculating portion 10, and the control parameter of the manipulator 2 is calculated on the basis of this shape information (step SA4). The manipulator control portion 3 controls the manipulator 2 on the basis of the control parameter calculated by the control-parameter calculating portion 10 (step SA5).

As has been described above, with the medical manipulator system 1 according to this embodiment, there is an advantage in that it is possible to precisely control the manipulator 2 by preventing the manipulator 2 from being unintentionally operated in the case of an error, shaking, or the like.

The driving of the shape sensors 4 by the shape-sensor driving portion 8, the estimation of the bent shape of the manipulator 2 by the shape estimating portion 6, and the calculation of the control parameter of the manipulator 2 by the control-parameter calculating portion 10 may be performed in real time.

As has been described above, as a result of estimating the shape of the manipulator 2 in real time and continuously calculating/updating the control parameter of the manipulator 2, it is possible to smoothly control the manipulator 2 even if the control parameter is changed.

For example, as a result of performing the driving of the shape sensors 4 by the shape-sensor driving portion 8, the estimation of the bent shape of the manipulator 2 by the shape estimating portion 6, and the calculation of the control parameter of the manipulator 2 by the control-parameter calculating portion 10 at a control period that is equal to or less than 10000 times the control period of the manipulator 2 of the manipulator control portion 3, for example, as a result of performing the shape estimation to the parameter calculation at a control period that is equal to or less than 1 s when the control period of the manipulator is 100 µs, it is possible to enhance the controllability of the manipulator 2.

The shape-sensor driving portion 8, the shape estimating portion 6, the control-parameter calculating portion 10, and the manipulator control portion 3 may be configured to be capable of individually being operated in separate, independent operating modes.

By employing such a configuration, for example, it is possible to switch between a parameter calculating mode in which the control of the manipulator 2 is not performed, and the control parameter of the manipulator 2 is calculated by detecting the shape information of the manipulator channel 13 by means of the shape sensors 4 and a manipulator controlling mode in which the detection of the shape information of the manipulator channel 13 and the control-parameter calculation are not performed, and treatment is performed by controlling the manipulator 2. Therefore, because the manipulator 2 is in a halted state in the parameter calculating mode, the manipulator 2 is not unnecessarily driven, and thus, it is possible to safely operate the manipulator 2.

Figure 6:
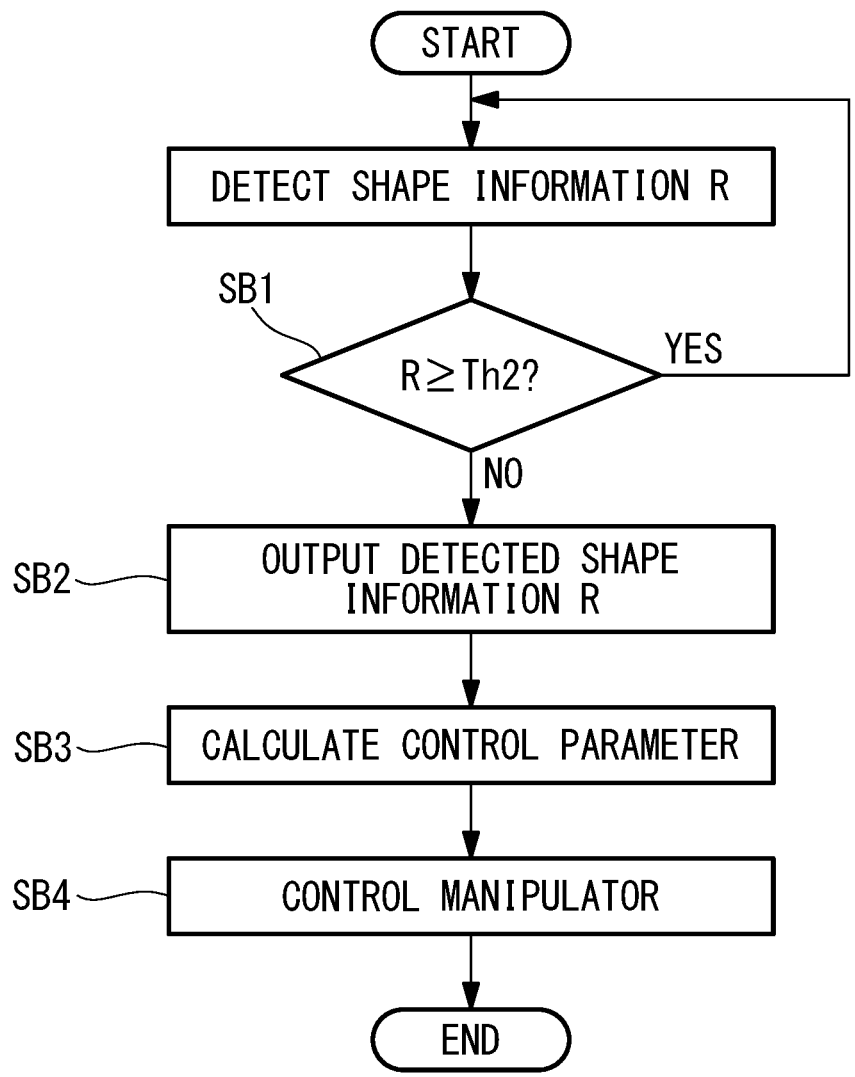
FIG. 6 is a flowchart showing another medical-manipulator controlling method according to the embodiment of the present invention.

In this embodiment, it may be determined that there is an abnormality in the case in which the shape information of the manipulator channel 13 detected by the shape sensors 4 is equal to or greater than a second threshold, and the shape estimating portion 6 may cause the shape sensors 4 to detect the shape information of the manipulator channel 13 again. Specifically, as shown in FIG. 6, in the case in which shape information R of the manipulator channel 13 detected by the shape sensors 4 is equal to or greater than the second threshold Th2, it is determined that there is some kind of abnormality, such as a position displacement that is inconceivable with normal use, and the shape estimating portion 6 causes the shape sensors 4 to detect the shape information of the manipulator channel 13 again (step SB1).

In the case in which the shape information R of the manipulator channel 13 detected by the shape sensors 4 is less than the second threshold Th2, it is determined that there is no abnormality such as a position displacement, and the detected shape information R is output to the control-parameter calculating portion (step SB2). The control-parameter calculating portion 10 calculates the control parameter of the manipulator 2 on the basis of the output shape information R (step SB3), and the manipulator control portion 3 controls the manipulator 2 on the basis of this calculated control parameter (step SB4).

As has been described above, with the medical manipulator system 1 according to this embodiment, it is possible to ensure safety by preventing the manipulator 2 from being unreasonably controlled and driven on the basis of an abnormal value.

In this embodiment, the manipulator control portion 3 may compare the control parameter of the manipulator 2 calculated by the control-parameter calculating portion 10 and the control parameter of the manipulator 2 calculated one cycle earlier, and, in the case in which the difference therebetween is equal to or greater than a third threshold, a corrected control parameter that is corrected by a high-frequency cut-off filter stored in the manipulator control portion 3 may be output to the manipulator driving portion 11.

Figure 7:
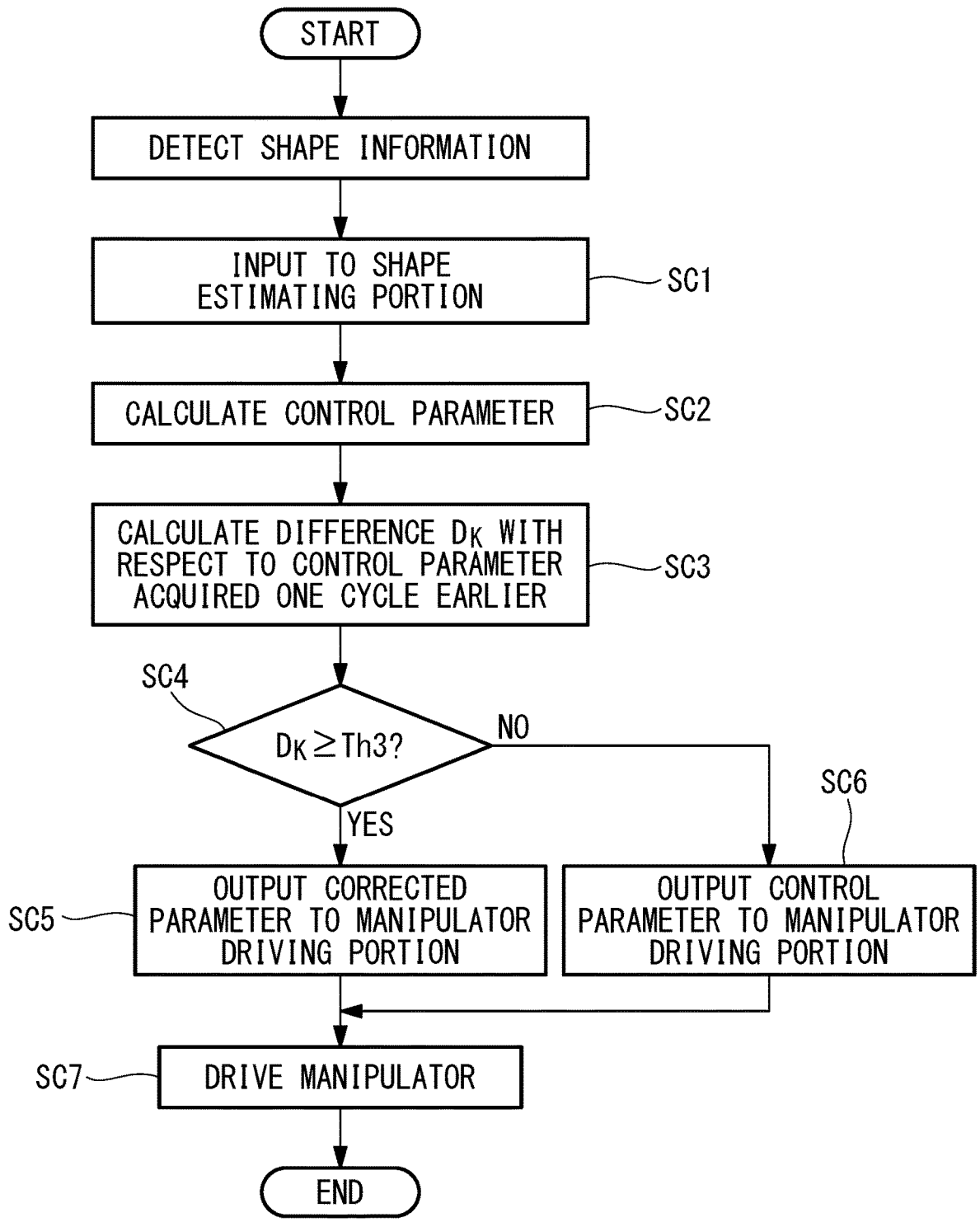
FIG. 7 is a flowchart showing another medical-manipulator controlling method according to the embodiment of the present invention.

Specifically, as shown in FIG. 7, the shape information of the manipulator channel 13 detected by the shape sensors 4 is output to the shape estimating portion 6 (step SC1), and the control parameter of the manipulator 2 is calculated by the control-parameter calculating portion 10 on the basis of this shape information (step SC2). Next, the manipulator control portion 3 compares the calculated control parameter and the control parameter of the manipulator 2 calculated one cycle earlier (step SC3), and, in the case in which this difference $D_k$ therebetween is equal to or greater than the third threshold Th3 (step SC4), the corrected control parameter that is corrected by the high-frequency cut-off filter stored in the manipulator control portion 3 is output to the manipulator driving portion 11 (step SC5). Then, the manipulator 2 is driven by the manipulator driving portion 11 on the basis of the corrected control parameter that has been corrected (step SC7).

In the case in which the difference $D_k$ between the calculated control parameter and the control parameter of the manipulator 2 calculated one cycle earlier is less than the third threshold Th3, the original control parameter is output to the manipulator driving portion 11 (step SC6), and the manipulator 2 is driven by the manipulator driving portion 11 on the basis of the output control parameter (step SC7).

As has been described above, with the medical manipulator system 1 according to this embodiment, because the manipulator 2 is driven on the basis of the corrected control parameter in the case in which the difference $D_k$ between the control parameter of the manipulator 2 and the control parameter of the manipulator 2 calculated one cycle earlier is equal to or greater than the third threshold Th3, it is possible to keep the driven amount of the manipulator 2 within a certain range even if the parameter is suddenly changed, and therefore, it is possible to stably drive the manipulator 2.

In this embodiment, the manipulator control portion 3 may compare the control parameter of the manipulator 2 calculated by the control-parameter calculating portion 10 and the control parameter of the manipulator 2 calculated one cycle earlier, may determine that there is an abnormality in the case in which the difference therebetween is greater than a fourth threshold Th4, and may cause the shape sensors 4 to detect the shape information of the manipulator channel 13 again.

Figure 8:
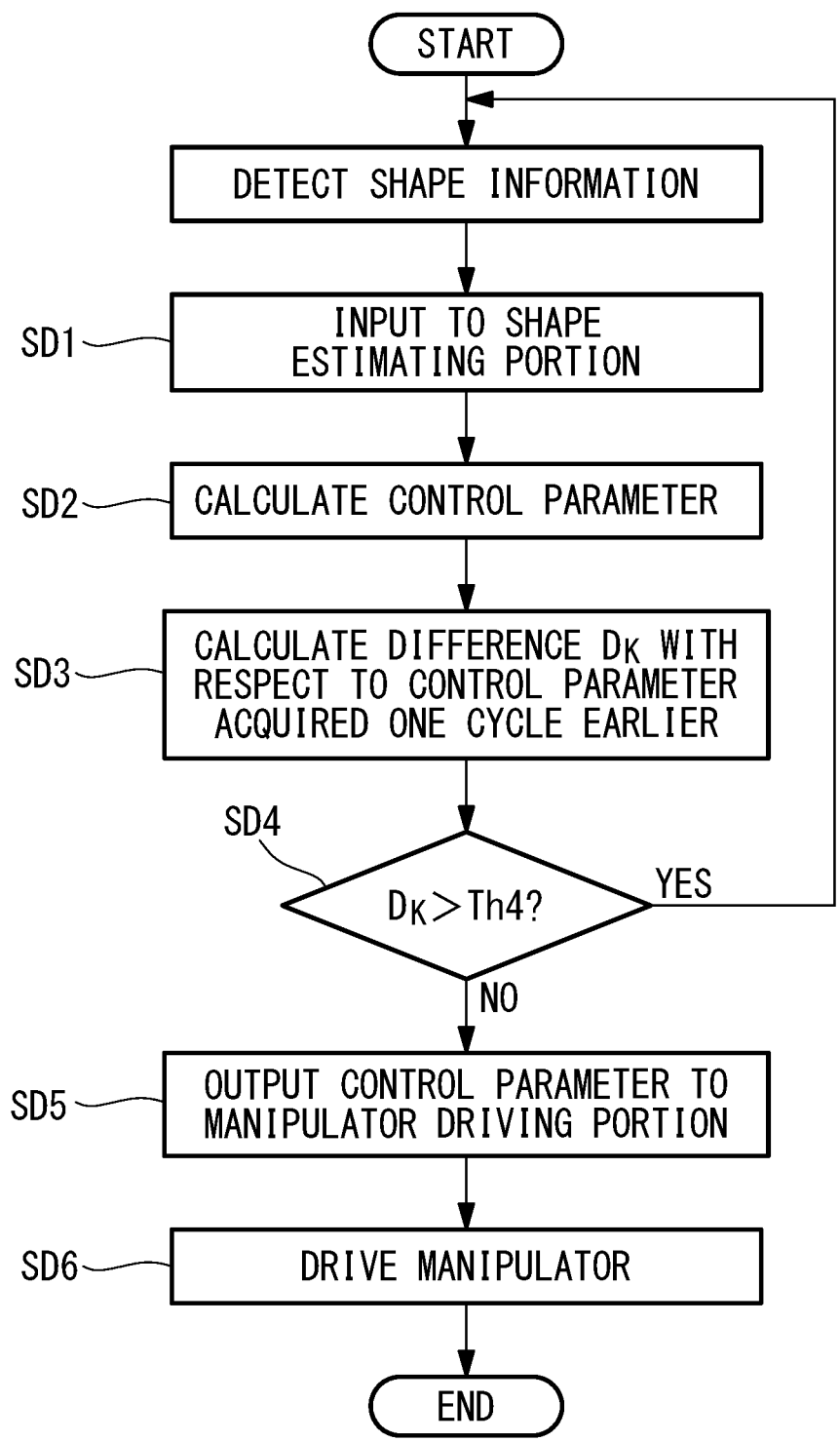
FIG. 8 is a flowchart showing another medical-manipulator controlling method according to the embodiment of the present invention.

Specifically, as shown in FIG. 8, the shape information of the manipulator channel 13 detected by the shape sensors 4 is output to the shape estimating portion 6 (step SD1), and the control parameter of the manipulator 2 is calculated by the control-parameter calculating portion 10 on the basis of this shape information (step SD2). Next, the manipulator control portion 3 compares the calculated control parameter and the control parameter of the manipulator 2 calculated one cycle earlier (step SD3), determines that there is an abnormality in the case in which the difference $D_k$ therebetween is greater than the fourth threshold Th4 (step SD4), and causes the shape sensors 4 to detect the shape information of the manipulator channel 13 again.

In the case in which the difference $D_k$ is equal to or less than the fourth threshold Th4, the original control parameter is output to the manipulator driving portion 11 (step SD5), and the manipulator 2 is driven by the manipulator driving portion 11 on the basis of the output control parameter (step SD6).

As has been described above, with the medical manipulator system 1 according to this embodiment, because it is determined that there is some kind of abnormality in the case in which the difference $D_k$ between the control parameter of the manipulator 2 and the control parameter of the manipulator 2 calculated one cycle earlier is greater than the fourth threshold Th4, it is possible to safely perform treatment by preventing the manipulator 2 from being unreasonably driven on the basis of an abnormal value.

This embodiment may be provided with a warning portion (not shown) that issues a warning to an operator indicating the occurrence of an abnormal state, by means of voice or the like, in the case in which the number of times the determination that there is an abnormality is detected reaches or exceeds a predetermined number of times.

By doing so, in the case in which there is some kind of abnormality, such as a position displacement that is inconceivable with normal use, it is possible to take measures so that the manipulator 2 is not unreasonably controlled and driven on the basis of an abnormal value.

In this embodiment, the manipulator driving portion 11 controls the joints 16 on the basis of the shape information of the manipulator 2 detected by the shape sensors 4.

Because the joints of the manipulator 2 are controlled on the basis of the shape information of the manipulator, it is possible to enhance the controllability of the angle of the distal-end portion of the manipulator 2.

Figure 4B:
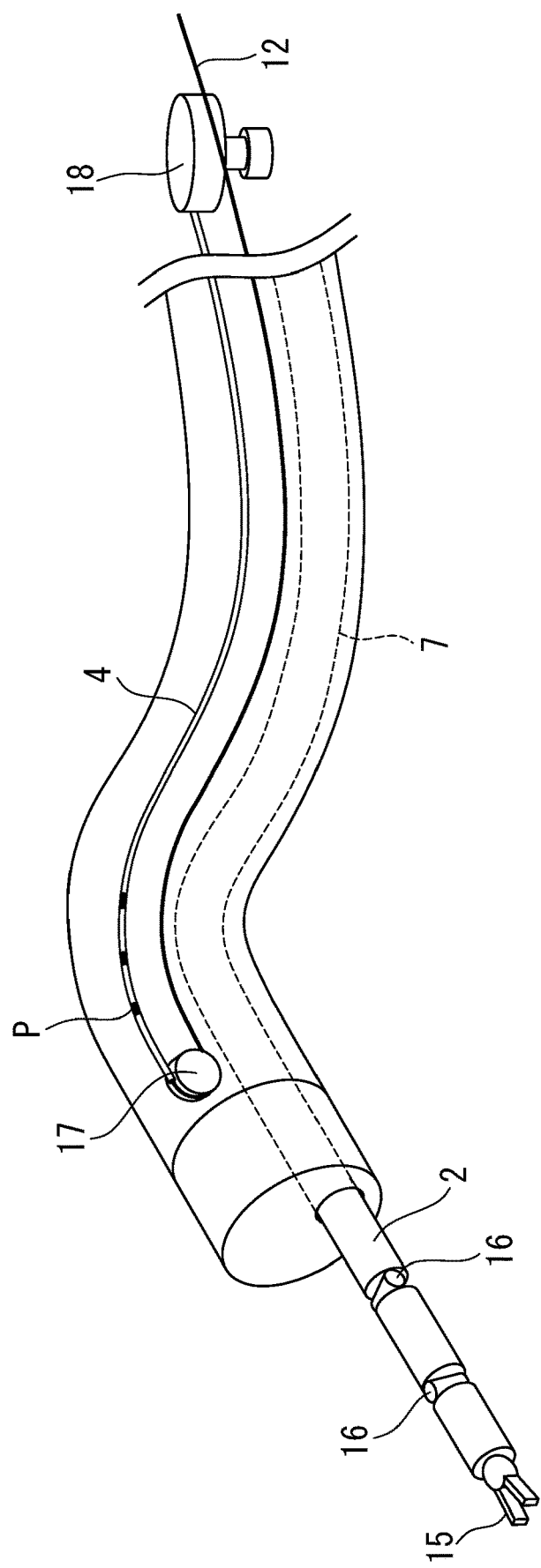
FIG. 4B is a diagram showing first modifications of the shape sensor and the shape-sensor driving portion in FIG. 4A.

Although this embodiment has been described in terms of an example in which the shape-sensor driving portion 8 is provided with the motor 18 disposed in the vicinity of the base end of the manipulator 2 and the guiding member 17 disposed in the vicinity of the distal end of the manipulator 2, and the shape sensors 4 formed in a loop shape are driven forward and backward between the motor 18 and the guiding member 17, alternatively, as a first modification, for example, as shown in FIG. 4B, a pulling wire 12 having a diameter that is smaller than those of the shape sensors 4 is connected to a distal end of a shape sensor 4, and a loop formed of the shape sensors 4 and the pulling wire 12 may be driven forward and backward between the motor 18 and the guiding member 17. By doing so, it is possible to prevent the shape sensors 4 from being folded and broken by winding the pulling wire 12 about the guiding member 17, and, it is possible to reduce the inner diameter of the route A into which the shape sensors 4 are inserted by employing the pulling wire having a diameter that is smaller than those of the shape sensors.

Figure 4C:
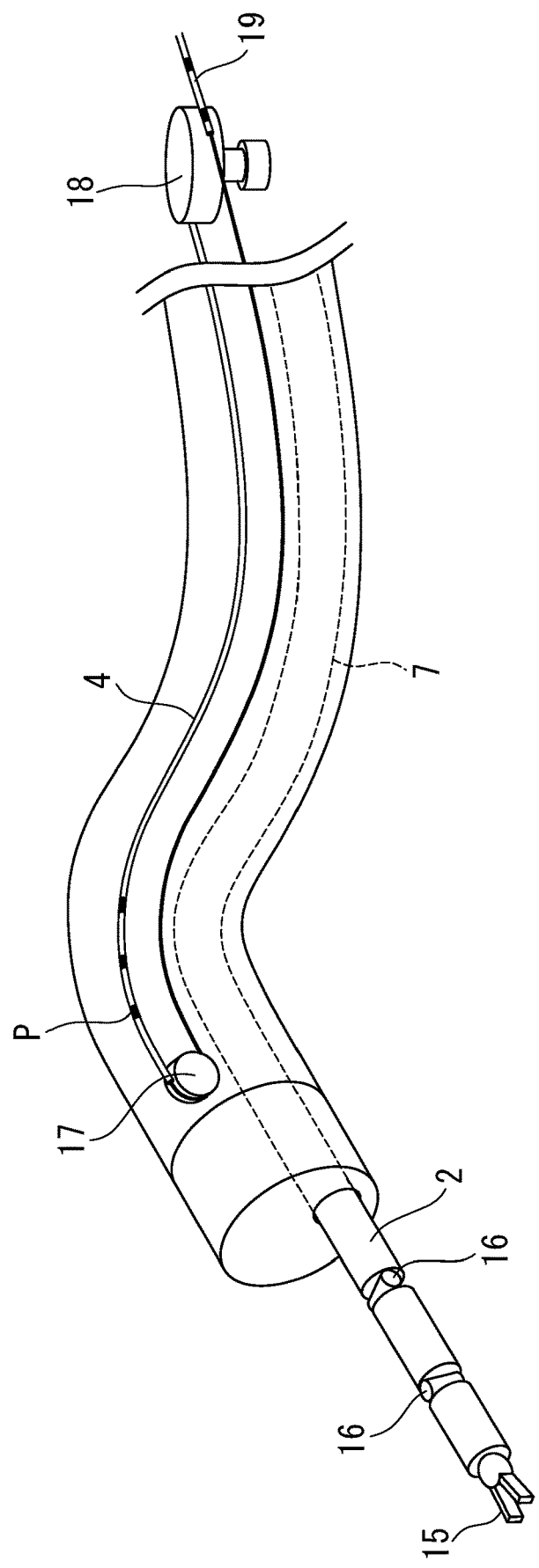
FIG. 4C is a diagram showing second modifications of the shape sensor and the shape-sensor driving portion in FIG. 4A.

As a second modification, as shown in FIG. 4C, a shape sensor 4 may be connected to one end of the pulling wire 12, an auxiliary shape sensor 19 that is disposed parallel to the shape sensor 4 may be connected to the other end of the pulling wire 12, and a loop formed by the shape sensor 4, the pulling wire 12, and the auxiliary shape sensor 19 may be driven forward and backward between the motor 18 and the guiding member 17. By doing so, because it is possible to simultaneously detect the shape information of the manipulator channel 13 in two directions by means of the two shape sensors, it is possible to more precisely and quickly estimate the bent shape of the manipulator 2.

Figure 4D:
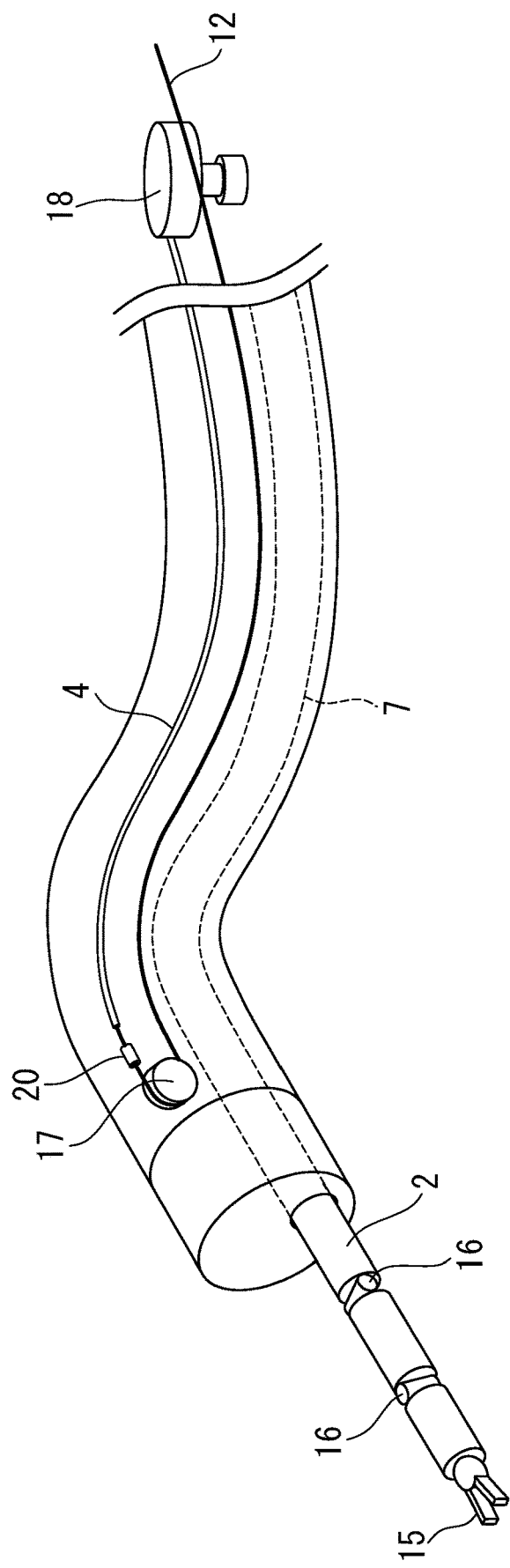
FIG. 4D is a diagram showing third modifications of the shape sensor and the shape-sensor driving portion in FIG. 4A.

As a third modification, as shown in FIG. 4D, a stopper 20 that prevents the shape sensor 4 from intruding into the guiding member 17 may be provided between the shape sensor 4 and the guiding member 17. By doing so, the shape sensor 4 is prevented from being wound about the guiding member 17, and thus, it is possible to prevent, with a simple configuration, the shape sensor 4 from being folded or broken.

Although FIG. 4D shows, as an example of the stopper 20, a cylinder having an inner diameter that is smaller than the outer diameter of the shape sensor 4, any member can be employed so long as the shape thereof is capable of preventing the distal end of the shape sensor 4 from intruding into the guiding member 17.

Figure 4E:
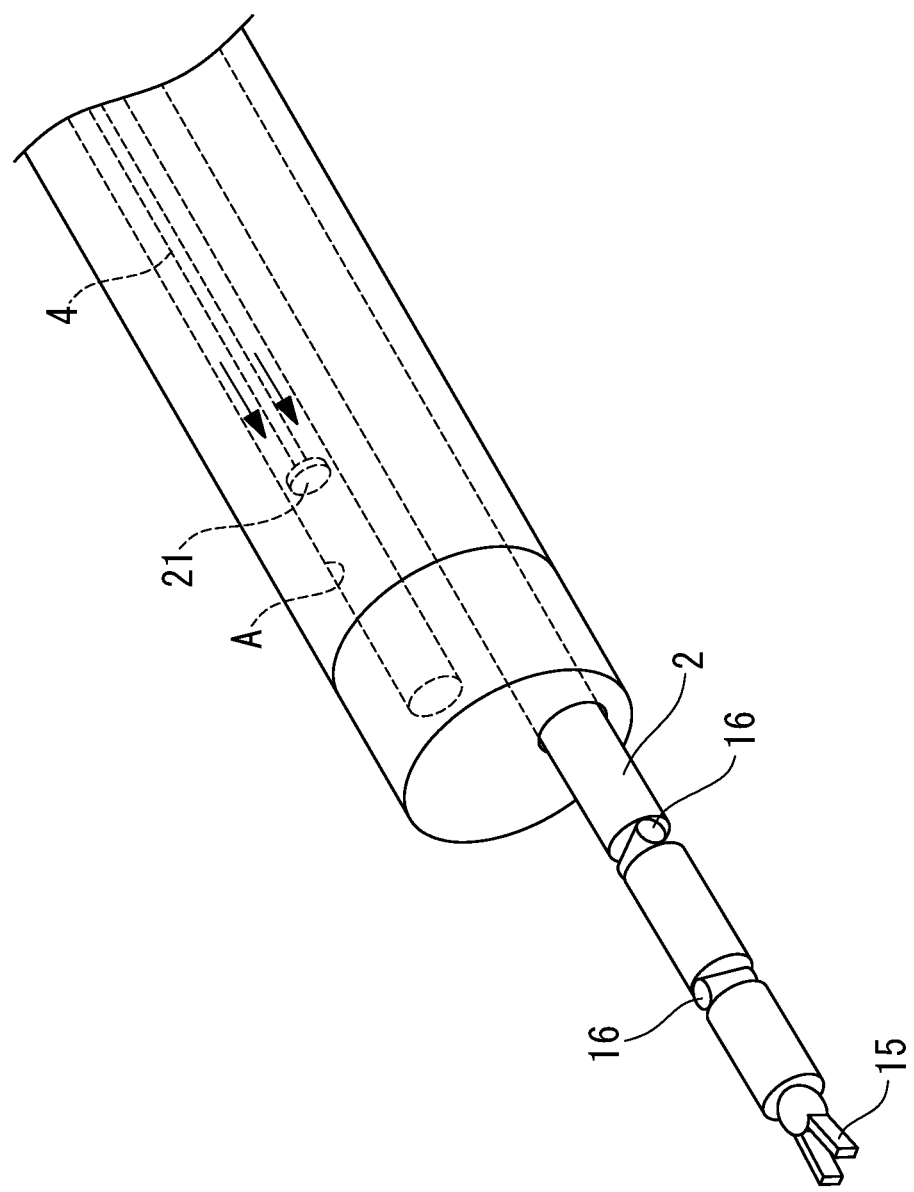
FIG. 4E is a diagram showing fourth modifications of the shape sensor and the shape-sensor driving portion in FIG. 4A.

As a fourth modification, as shown in FIG. 4E, a pressure-receiving member 21 that is formed of, for example, a balloon or the like, and that is expandable to substantially the same diameter as the inner diameter of the route A may be provided at the distal end of the shape sensor 4, and, instead of the shape-sensor driving portion 8 formed of the motor 18 and the guiding member 17, a pressuring member 22 for causing the shape sensors 4 to be driven forward and backward by applying pressure to the pressure-receiving member 21 in the longitudinal direction may be provided. As the pressuring member 22, it is possible to employ a pump or the like that imparts a propulsive force to a pressure-receiving member 21 by applying hydraulic pressure, pneumatic pressure, or the like thereto.

As a result of applying the pressure from the pressuring member to the pressure-receiving member 21, it is possible to easily drive the shape sensors 4 forward and backward in the longitudinal direction even in the case in which the shape sensors 4 are formed of a flexible material or the like. Because it is possible to reduce the inner diameter of the route A as compared with a system in which the shape-sensor driving portion 8 is formed of the guiding member 17 and the motor 18, it is possible to reduce the diameter of the medical manipulator system 1.

As a result, the following aspect is read from the above described embodiment of the present invention.

An aspect of the present invention is a medical manipulator system including: an elongated manipulator that has a flexible portion and that has one or more joints at a distal end; a manipulator channel that passes through the manipulator; a route that is provided in the manipulator channel along a longitudinal direction; a shape sensor that is provided so as to be capable of moving in an interior of the route, and that has one or more detection points that detect shape information of the manipulator channel; a shape-sensor driving portion that causes the shape sensor to be driven forward and backward along the longitudinal direction of the route; a manipulator driving portion that drives the manipulator; and a controller that controls the manipulator and the shape sensor, wherein the controller is provided with a positional-information calculating portion that calculates longitudinal-direction positional information of the shape sensor on the basis of a driven amount of the shape-sensor driving portion, a shape estimating portion that estimates a bent shape of the manipulator on the basis of the detected shape information of the manipulator channel and the calculated longitudinal-direction positional information of the shape sensor, a control-parameter calculating portion that calculates a control parameter of the manipulator from the estimated bent-shape information of the manipulator, and a manipulator controller that controls the manipulator on the basis of the calculated control parameter.

With this aspect, as a result of the shape sensor, which has one or more detection points, being inserted into the route provided along the longitudinal direction of the manipulator channel in which the elongated manipulator having the flexible portion is disposed and the shape of the manipulator channel being detected by the shape sensor while the shape sensor is driven forward and backward along the longitudinal direction of the route, it is possible to estimate the bent shape of the manipulator on the basis of the detected shape of the manipulator channel and the longitudinal-direction positional information thereof. In other words, because it is possible to detect the shape at the respective positions in the longitudinal direction by driving, in real time, a small number of shape sensors forward and backward while performing a procedure, it is possible to estimate the shape of the manipulator channel, that is, the bent shape of the manipulator in the longitudinal direction when being disposed in the manipulator channel by using a minimum number of shape sensors without having to employ a shape sensor such as a fiber bundle in which numerous optical fibers are bundled.

Because the shape sensor has one or more detection points, it is possible to detect multiple items of the route information as a result of a minimum amount of movement.

Because the manipulator is controlled on the basis of the calculated control parameter by calculating the control parameter of the manipulator with the control-parameter calculating portion from the information concerning the estimated bent shape of the manipulator, it is possible to achieve good control of the manipulator regardless of the shape of the flexible portion by compensating for the attenuation of the driving force of the manipulator and interference of the joints.

In the above-described aspect, the shape estimating portion may compare the shape information of the manipulator channel detected by the shape sensor and the shape information of the same manipulator channel detected (N+1) cycles (N≥0) earlier, and may update the shape information of the manipulator in the case in which the difference therebetween is equal to or greater than a first threshold.

By doing so, because the detected shape information of the manipulator channel and the shape information of the manipulator channel detected in advance are compared and the shape information of the manipulator is updated only in the case in which the difference therebetween is equal to or greater than the first threshold, it is possible to precisely control the manipulator by preventing the manipulator from being unintentionally operated in the case of an error, shaking, or the like.

In the above-described aspect, the shape-sensor driving portion may be provided with: a motor that is disposed in the vicinity of a base end of the manipulator and that generates a motive power for driving, by means of rotational driving thereof, the shape sensor forward and backward; and a guiding member that is disposed in the vicinity of a distal end of the manipulator and that guides the shape sensor by winding a portion thereof about the guiding member, wherein the shape sensor may be moved forward and backward by pulling and feeding out the shape sensor in association with the rotational driving of the motor.

By doing so, the shape sensor becomes capable of being driven forward and backward between the motor disposed in the vicinity of the base end of the manipulator and the guiding member disposed in the vicinity of the distal end of the manipulator in the route provided parallel to the manipulator channel. Therefore, it is possible to estimate the bent shape of the manipulator over the entire length of the manipulator (in particular, the flexible portion) disposed in the manipulator channel. Because it is possible to drive the shape sensor forward and backward in the route disposed parallel to the manipulator channel even when a procedure is being performed by using the manipulator, it is possible to estimate the bent shape of the manipulator in real time while the procedure is being performed.

In the above-described aspect, a pulling wire having a diameter that is smaller than that of the shape sensor may be connected to a distal end of the shape sensor, and the shape-sensor driving portion may be provided with: a motor that is disposed in the vicinity of a base end of the manipulator and that generates a motive power for driving the shape sensor forward and backward via the pulling wire by means of the rotational driving thereof, and a guiding member that is disposed in the vicinity of a distal end of the manipulator and that guides the pulling wire by winding a portion thereof about the guiding member, wherein the shape sensor may be moved forward and backward by pulling and feeding out the shape sensor in association with the rotational driving of the motor.

By doing so, the shape sensor becomes capable of being driven forward and backward between the motor disposed in the vicinity of the base end of the manipulator and the guiding member disposed in the vicinity of the distal end of the manipulator in the route provided parallel to the manipulator channel. At this time, the pulling wire is connected to the distal end of the shape sensor, and a portion of this pulling wire is wound about the guiding member. Therefore, because the shape sensor is not wound about the guiding member, it is possible to prevent the shape sensor from being folded and broken. Because the pulling wire has a diameter that is smaller than that of the shape sensor, it is possible to reduce the diameter of a bent portion of the guiding member. Therefore, it is possible to reduce the inner diameter of the route into which the shape sensor is inserted, and thus, it is possible to reduce the size of the medical manipulator system.

The above-described aspect may be provided with an auxiliary shape sensor that is disposed parallel to the shape sensor and that is connected to an end portion of the pulling wire on the opposite side from the side at which the shape sensor is connected.

By doing so, with the two shape sensors, namely, the shape sensor having one or more detection points and the auxiliary shape sensor, it is possible to simultaneously detect the shape information of the manipulator channel in two directions at the respective positions in the longitudinal direction of the route, and thus, it is possible to more precisely and quickly estimate the bent shape of the manipulator, The above-described aspect may be provided with, between the shape sensor and the guiding member, a stopper that prevents the shape sensor from intruding into the guiding member.

By doing so, it is possible to prevent the shape sensor from being wound about the guiding member, and it is possible to prevent, in a simple manner, the shape sensor from being folded and broken.

The above-described aspect may be provided with a pressure receiving member that is provided at a distal end of the shape sensor and that is capable of expanding to substantially the same diameter as the inner diameter of the route, wherein the shape-sensor driving portion may be provided with a pressuring member for driving the shape sensor forward and backward by applying pressure to the pressure receiving member in the longitudinal direction.

By doing so, it is possible to easily drive the shape sensor forward and backward in the longitudinal direction as a result of applying, by means of the pressuring member, pressure in the longitudinal direction to the pressure receiving member provided at the distal end of the shape sensor even in the case in which the shape sensor is formed of a flexible material.

As compared with the structure in which the shape sensor is driven by a motor and a guiding member that guides the shape sensor by winding a portion of the shape sensor about the guiding member, it is possible to reduce the inner diameter of the route into which the shape sensor is inserted, and therefore, it is possible to reduce the size of the medical manipulator system.

In the above-described aspect, the shape estimating portion may determine that there is an abnormality in the case in which the shape information of the manipulator channel detected by the shape sensor is equal to or greater than a second threshold; and may cause the shape sensor to detect the shape information of the manipulator channel again.

By doing so, in the case in which the shape information of the manipulator channel is equal to or greater than the second threshold, it is determined that there is some kind of abnormality, such as a position displacement that is inconceivable with normal use, and the shape sensor is made to detect the shape information of the manipulator channel again. Therefore, it is possible to ensure safety by preventing the manipulator from being unreasonably controlled and driven on the basis of an abnormal value.

In the above-described aspect, the manipulator controller may compare the control parameter of the manipulator calculated by the control-parameter calculating portion and the control parameter of the manipulator calculated one cycle earlier; and, in the case in which the difference therebetween is equal to or greater than a third threshold, may cause the manipulator driving portion to output a corrected control parameter that is corrected by a high-frequency cut-off filter stored in the manipulator controller.

By doing so, because the manipulator is driven on the basis of the corrected control parameter corrected by the high-frequency cut-off filter in the case in which the difference between the control parameter of the manipulator and the control parameter of the manipulator calculated one cycle earlier is equal to or greater than the third threshold, it is possible to keep the driven amount of the manipulator within a certain range. Therefore, it is possible to stably drive the manipulator by avoiding destabilization of the manipulator operation due to a sudden change in the parameter.

In the above-described aspect, the manipulator controller may compare the controller of the manipulator calculated by the control-parameter calculating portion and the control parameter of the manipulator calculated one cycle earlier; and, in the case in which the difference therebetween is greater than a fourth threshold, may determine that there is an abnormality, and may cause the shape sensor to detect the shape information of the manipulator channel again.

By doing so, because it is determined that some kind of abnormality is occurring in the case in which the difference between the control parameter of the manipulator and the control parameter of the manipulator calculated one cycle earlier is greater than the fourth threshold, it is possible to prevent the manipulator from being unreasonably controlled on the basis of an abnormal value, and thus, it is possible to safely operate the manipulator The above-described aspect may be provided with a warning portion that issues a warning to an operator indicating the occurrence of an abnormal state in the case in which the number of times the determination that there is an abnormality is detected reaches or exceeds a predetermined number of times.

By doing so, it is possible to reliably make an operator recognize the occurrence of an abnormality, visibly, audibly, or the like in the case in which the number of times an abnormality is detected reaches or exceeds a predetermined number of times, and thus, it is possible to increase safety.

In the above-described aspect, the manipulator driving portion may control the joints on the basis of the shape information of the manipulator acquired by the shape sensor.

By doing so, because the joints of the manipulator are controlled on the basis of the shape information of the flexible portion of the manipulator, it is possible to enhance the controllability of the angles of the distal-end portion of the manipulator.

An aspect of the present invention is a bent-shape estimating method for a medical manipulator, said method including: a shape-sensor driving step of moving a shape sensor having one or more detection points forward and backward along a longitudinal direction of a manipulator channel in which an elongated manipulator that has a flexible portion having one or more joints at a distal end thereof is disposed; a positional-information calculating step of calculating longitudinal-direction positional information of the shape sensor on the basis of a driven amount of the shape sensor; and a shape estimating step of estimating the bent shape of the manipulator on the basis of the detected shape information of the shape sensor and the shape information of the manipulator channel detected by the shape sensor at the calculated longitudinal-direction positions of the shape sensor.

An aspect of the present invention is a controlling method for a medical manipulator, said method including: a control-parameter calculating step of calculating a control parameter of a manipulator from the bent shape of the manipulator estimated by means of the bent-shape estimating method for a medical manipulator according to claim 13; and a manipulator controlling step of controlling the manipulator on the basis of the calculated control parameter.

REFERENCE SIGNS LIST 1 medical manipulator system
2 manipulator
3 manipulator controller (manipulator control portion)
4 shape sensor
5 overtube
6 shape estimating portion
7 flexible portion
8 shape-sensor driving portion
9 positional-information calculating portion
10 control-parameter calculating portion
11 manipulator driving portion
12 pulling wire
13 manipulator channel
14 endoscope channel
15 treating portion
16 joint
17 guiding member (shape-sensor driving portion)
18 motor (shape-sensor driving portion)
19 auxiliary shape sensor
20 stopper
21 pressure receiving member
22 pressuring member
100 controller (control portion)
A route
P detection point

The invention claimed is:

1. A medical manipulator system comprising:
an elongated manipulator that has a flexible portion and that has one or more joints at a distal end;
a manipulator channel that passes through the manipulator;
a route that is provided in the manipulator channel along a longitudinal direction;
a shape sensor that is provided so as to move in an interior of the route, and that has one or more detection points that is configured to detect shape information of the manipulator channel;
a shape-sensor driving portion that is configured to cause the shape sensor to be driven forward and backward along the longitudinal direction of the route;
a manipulator driving portion that is configured to drive the manipulator; and
a controller that is configured to control the manipulator and the shape sensor,
wherein the controller is provided with a one or more processors, the one or more processors are configured to:
calculate longitudinal-direction positional information of the shape sensor on the basis of a driven amount of the shape-sensor driving portion,
estimate a bent shape of the manipulator on the basis of the detected shape information of the manipulator channel and the calculated longitudinal-direction positional information of the shape sensor,
calculate a control parameter of the manipulator from the estimated bent-shape information of the manipulator, and
a manipulator controller that controls the manipulator on the basis of the calculated control parameter.

2. A medical manipulator system according to claim 1, wherein the one or more processors compare the shape information of the manipulator channel detected by the shape sensor and the shape information of the same manipulator channel detected (N+1) cycles (N≥0) earlier, and updates the shape information of the manipulator in the case in which the difference therebetween is equal to or greater than a first threshold.

3. A medical manipulator system according to claim 1, wherein the shape-sensor driving portion is provided with:
a motor that is disposed in the vicinity of a base end of the manipulator and that is configured to generate a motive power for driving, by means of rotational driving thereof, the shape sensor forward and backward; and
a guiding member that is disposed in the vicinity of a distal end of the manipulator and that is configured to guide the shape sensor by winding a portion thereof about the guiding member,
wherein the shape sensor is moved forward and backward by pulling and feeding out the shape sensor in association with the rotational driving of the motor.

4. A medical manipulator system according to claim 1 wherein a pulling wire having a diameter that is smaller than that of the shape sensor is connected to a distal end of the shape sensor, and
the shape-sensor driving portion is provided with:
a motor that is disposed in the vicinity of a base end of the manipulator and that is configured to generate a motive power for driving the shape sensor forward and backward via the pulling wire by means of the rotational driving thereof, and
a guiding member that is disposed in the vicinity of a distal end of the manipulator and that is configured to guide the pulling wire by winding a portion thereof about the guiding member, wherein the shape sensor is moved forward and backward by pulling and feeding out the shape sensor in association with the rotational driving of the motor.

5. A medical manipulator system according to claim 4, further comprising:
an auxiliary shape sensor that is disposed parallel to the shape sensor and that is connected to an end portion of the pulling wire on the opposite side from the side at which the shape sensor is connected.

6. A medical manipulator system according to claim 4, further comprising:
between the shape sensor and the guiding member, a stopper that is configured to prevent the shape sensor from intruding into the guiding member.

7. A medical manipulator system according to claim 1, further comprising:
a pressure receiving member that is provided at a distal end of the shape sensor and that is configured to expand to substantially the same diameter as the inner diameter of the route,
wherein the shape-sensor driving portion is provided with a pressuring member that is configured to drive the shape sensor forward and backward by applying pressure to the pressure receiving member in the longitudinal direction.

8. A medical manipulator system according to claim 1, wherein the one or more processors determine that there is an abnormality in the case in which the shape information of the manipulator channel detected by the shape sensor is equal to or greater than a second threshold; and causes the shape sensor to detect the shape information of the manipulator channel again.

9. A medical manipulator system according to claim 1, wherein the one or more processors compare the calculated control parameter of the manipulator and the control parameter of the manipulator calculated one cycle earlier; and, in the case in which the difference therebetween is equal to or greater than a third threshold, causes the manipulator driving portion to output a corrected control parameter that is corrected by a high-frequency cut-off filter stored in the controller.

10. A medical manipulator system according to claim 1, wherein the one or more processors compare the calculated control parameter of the manipulator and the control parameter of the manipulator calculated one cycle earlier; and, in the case in which the difference therebetween is greater than a fourth threshold, determines that there is an abnormality, and causes the shape sensor to detect the shape information of the manipulator channel again.

11. A medical manipulator system according to claim 8, further comprising:
a warning portion that is configured to issue a warning to an operator indicating the occurrence of an abnormal state in the case in which the number of times the determination that there is an abnormality is detected reaches or exceeds a predetermined number of times.

12. A medical manipulator system according to claim 1, wherein the manipulator driving portion controls the joints on the basis of the shape information of the manipulator acquired by the shape sensor.

13. A bent-shape estimating method for a medical manipulator, said method comprising:
a shape-sensor driving step of moving a shape sensor having one or more detection points forward and backward along a longitudinal direction of a manipulator channel in which an elongated manipulator that has a flexible portion having one or more joints at a distal end thereof is disposed;
a positional-information calculating step of calculating longitudinal-direction positional information of the shape sensor on the basis of a driven amount of the shape sensor; and
a shape estimating step of estimating the bent shape of the manipulator on the basis of the detected shape information of the shape sensor and the shape information of the manipulator channel detected by the shape sensor at the calculated longitudinal-direction positions of the shape sensor.

14. A controlling method for a medical manipulator, said method comprising:
a control-parameter calculating step of calculating a control parameter of a manipulator from the bent shape of the manipulator estimated by means of the bent-shape estimating method for a medical manipulator according to claim 13; and
a manipulator controlling step of controlling the manipulator on the basis of the calculated control parameter.

* * * * *